United States Patent [19]

Lee et al.

[11] Patent Number: 5,415,659
[45] Date of Patent: May 16, 1995

[54] SPINAL FIXATION SYSTEM AND PEDICLE CLAMP

[75] Inventors: Casey K. Lee, Roseland, N.J.; Erik J. Wagner, Allen, Tex.

[73] Assignee: AMEI Technologies Inc., Wilmington, Del.

[21] Appl. No.: 160,393

[22] Filed: Dec. 1, 1993

[51] Int. Cl.⁶ .................................................. A61B 17/56
[52] U.S. Cl. ............................................. 606/61; 81/426; 81/419; 24/569; 269/156; 248/316.4
[58] Field of Search ................ 606/61, 60, 59, 72, 606/74, 53, 69, 104, 86, 105, 205, 207, 208; 81/424.5, 426, 426.5, 419, 420, 421–424; 24/514, 569; 248/231.4, 316.4; 269/251, 156, 266, 265, 269, 270

[56] References Cited

U.S. PATENT DOCUMENTS

| | | | |
|---|---|---|---|
| 1,686,640 | 10/1928 | Pierce, Jr. | 81/423 |
| 3,428,306 | 2/1969 | Harrison | 269/269 |
| 4,169,395 | 10/1979 | Hoskinson | 81/436 |
| 4,269,178 | 5/1981 | Keene . | |
| 4,422,451 | 12/1983 | Kalamchi . | |
| 4,433,676 | 2/1984 | Bobechko . | |
| 4,569,338 | 2/1986 | Edwards . | |
| 4,611,582 | 9/1986 | Duff . | |
| 4,655,218 | 4/1987 | Kulik et al. | 606/86 |
| 4,854,304 | 8/1989 | Zielke . | |
| 5,000,165 | 3/1991 | Watanabe . | |
| 5,005,562 | 4/1991 | Cotrel . | |
| 5,007,909 | 4/1991 | Rogozinski | 606/61 |
| 5,074,864 | 12/1991 | Gozad et al. | 606/54 |
| 5,092,893 | 3/1992 | Smith | 606/61 |
| 5,102,412 | 4/1992 | Rogozinski | 606/61 |
| 5,147,359 | 9/1992 | Cozad et al. | 606/61 |
| 5,176,678 | 1/1993 | Tsou | 606/61 |
| 5,201,734 | 4/1993 | Cozad et al. | 606/62 |
| 5,242,445 | 9/1993 | Ashman | 606/61 |
| 5,257,993 | 11/1993 | Asher et al. | 606/61 |
| 5,261,913 | 11/1993 | Marnay | 606/61 |
| 5,263,954 | 11/1993 | Schlapfer et al. | 606/61 |

*Primary Examiner*—Tamara L. Graysay
*Attorney, Agent, or Firm*—Baker & Botts

[57] ABSTRACT

A spinal fixation system is provided with pedicle clamps having multiple hooks for engagement with selected portions of a patient's vertebrae. The pedicle clamp includes three hooks which may be slidably positioned relative to each other to securely engage exterior surfaces of the lamina. A surgical tool is also provided to securely position the hooks with respect to each other on the exterior of the lamina. The surgical tool includes a fork for engaging the movable hooks of the pedicle clamp and a wrench for locking the movable hooks relative to each other and the pedicle clamp.

27 Claims, 4 Drawing Sheets

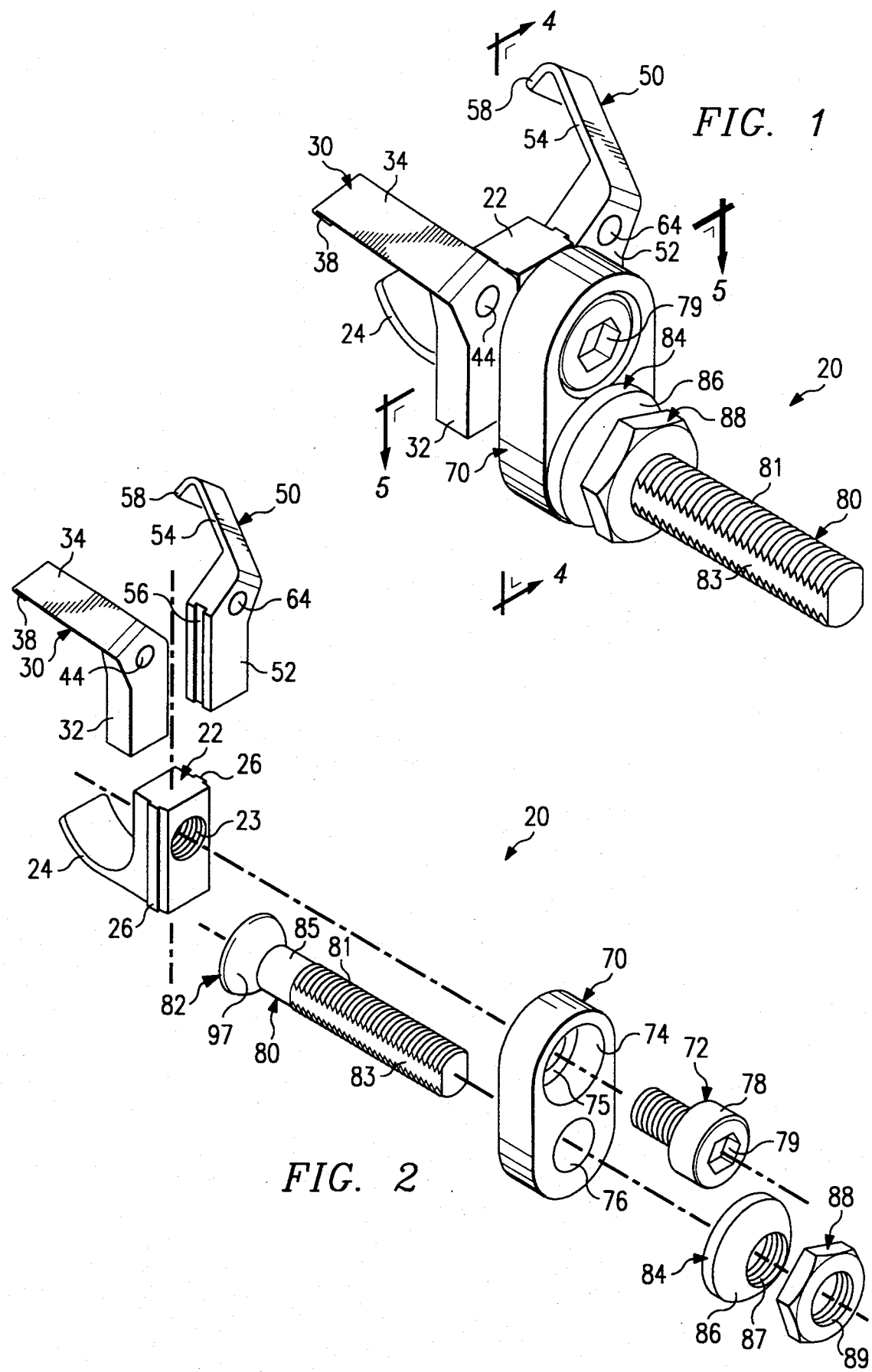

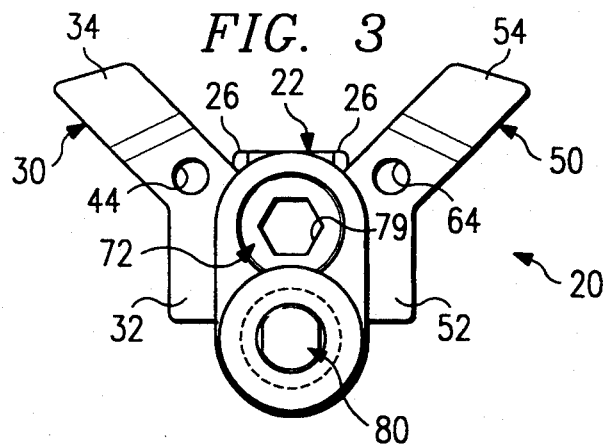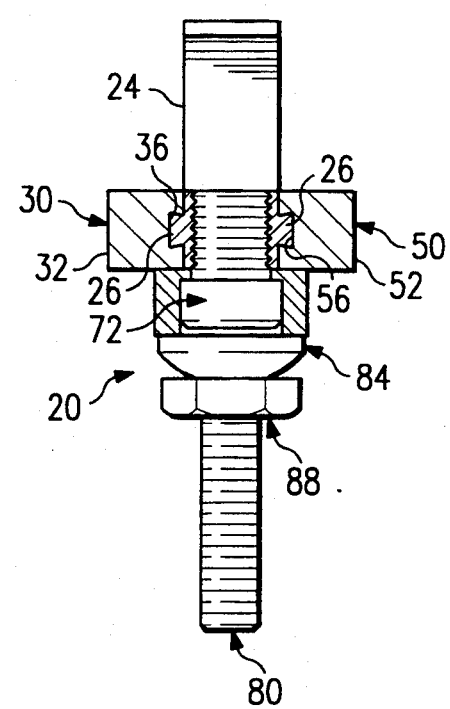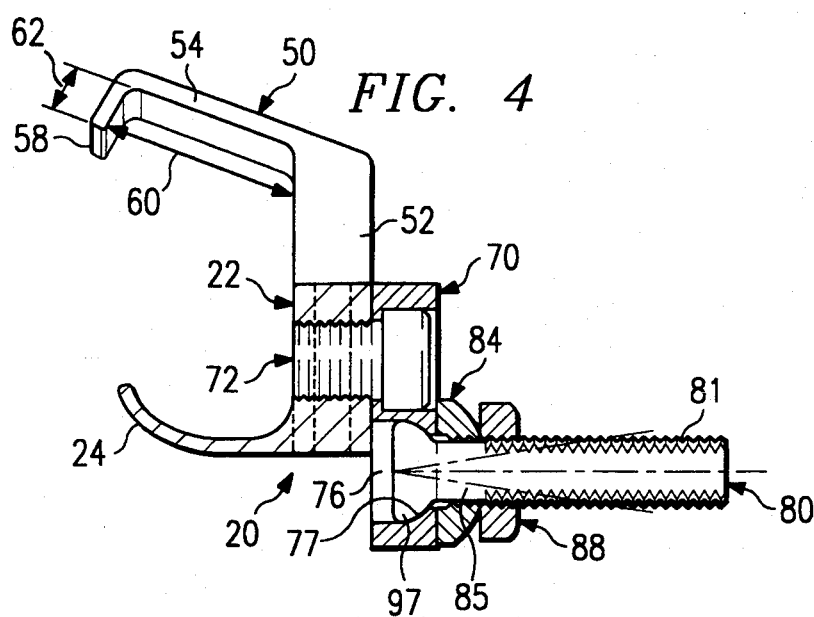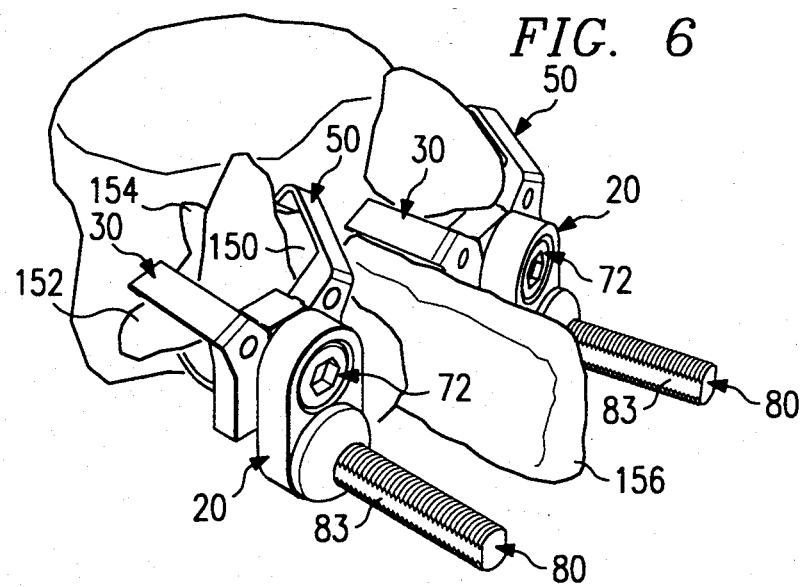

SPINAL FIXATION SYSTEM AND PEDICLE CLAMP

TECHNICAL FIELD OF THE INVENTION

This invention relates to surgical tools and medical constructs and more particularly relates to pedicle clamps used with spinal fixation equipment and methods for moving vertebrae to a desired relationship with respect to each other and maintaining the desired relationship.

BACKGROUND OF THE INVENTION

Spinal interlamellar fixation including lumbar sacral fusion and correcting scoliotic curves are well known and frequently used medical procedures. Spinal fixation systems used to correct problems in the lumbar and thoracic portion of the spine, are frequently installed posteriorly on opposite sides of the spinous process and adjacent to the transverse process. Such systems often include spinal instrumentation having connective structures such as a pair of plates and/or rods which are placed on opposite sides of the portion of the spinal column which is intended to be fused.

Pedicle, lateral and oblique mounting means may be used to secure the spinal instrumentation relative to the desired portion of the spine which will be fused by the fixation system. Screws, hooks, clamps and claws have been designed to attach spinal instrumentation to selected vertebrae of the spine. Cross-linking of the spinal instrumentation is designed to prevent migration of the rods or plates and to increase stiffness of the associated medical construct. Even with rigid cross-linking all spinal instrumentation is designed to provide only temporary fixation until solid bone fusion has been completed. Without adequate bone fusion, fatigue endurance of the spinal instrumentation may be exceeded and cause fracture of the rods or plates used with the medical construct.

Various types of pedicle screws, lamina clamps and vertebra hooks or claws have been used to attach spinal rods and spinal plates at desired locations adjacent to a patient's spine. Examples of spinal clamps and hooks are shown in U.S. Pat. Nos. 5,007,909; 5,074,864; 5,102,412; and 5,147,359 for use in fusing selected portions of a patient's spinal column. These patents are incorporated by reference for all purposes within this application.

Many of the presently available spinal hooks and clamps require assembly of small components while conducting the surgical procedure to attach the hook or clamp to portions of the vertebrae. Presently available spinal fixation systems frequently require careful alignment of the hardware used to connect the components of the spinal instrumentation with each other.

Presently available clamps generally engage the lamina adjacent to a pedicle in only two locations. Vertebra hooks and clamps generally have only one or two points of contact with the lamina. Prior spinal fixation systems which have only one or two points of contact with the lamina tend to move laterally relative to the pedicle and associated vertebra. Since pedicles have a generally elliptical cross section with tapered exterior surfaces, clamping a pedicle is similar to attempting to clamp a cone. Three points of contact are desirable for secure engagement with the selected vertebrae.

A need has thus arisen for improved pedicle clamps to attach spinal instrumentation to selected portion of a patient's spine without requiring additional manipulation of the spinal instrumentation and to minimize the use of pedicle screws while at the same time reducing requirements to assemble small pieces of hardware during the surgical procedure.

SUMMARY OF THE INVENTION

In accordance with the present invention, the disadvantages and problems associated with previous vertebra hooks, clamps, claws and related spinal fixation equipment have been substantially reduced or eliminated. The present invention allows a surgeon to install spinal instrumentation using pedicle clamps without having to position the spinal instrumentation at a specific distance relative to the vertebrae of the spine and without having to install additional hardware prior to connecting the pedicle clamp with portions of the patient's vertebrae. Pedicle clamps of the present invention allow attaching spinal instrumentation to selected portions of the patient's vertebrae with the pedicle clamps having different spacial relationships relative to each other.

A significant technical advantage of the present invention is that the pedicle clamp is installed as a fully assembled unit during the surgical procedure. The pedicle clamp allows a surgeon to control the attachment of a medical construct to the pedicles of lumbar and thoracic vertebrae without drilling holes, tapping, and inserting screws into the pedicle. A spinal fixation system using pedicle clamps in accordance with the present invention minimizes and substantially reduces clinical problems associated with pedicle screws.

Another significant advantage of the present invention is that the pedicle clamp provides the functional equivalent of a pedicle screw with respect to strength, durability, and versatility without having to drill and tap the pedicle itself. Pedicle clamps manufactured in accordance with the present invention provide three points of contact with the pedicle portion of selected vertebrae. By having three points of contact, the pedicle clamps ensure that the medical construct is securely attached to the pedicle and associated vertebrae without the use of pedicle screws.

In accordance with one aspect of the present invention, a pedicle clamp with three hooks is provided to attach spinal instrumentation to selected portions of a patient's vertebrae. Two of the hooks are slidable relative to each other and relative to a fixed hook. A surgical tool is provided to securely anchor the three hooks with selected portions of the patient's vertebrae and to releasably secure the three hooks relative to each other. The pedicle clamp also includes an adjustable connector which may be positioned relative to the hooks and secured in the desired position. A bridge screw or connecting post is carried by the connector to allow limited rotation and angular positioning of the bridge screw relative to the connector and the hooks.

BRIEF DESCRIPTION OF THE DRAWINGS

For a more complete understanding of the present invention, and the advantages thereof, reference is now made to the following description taken in conjunction with the accompanying drawings in which:

FIG. 1 is an isometric pictorial showing a pedicle clamp incorporating the present invention;

FIG. 2 is an isometric pictorial with portions broken away and other portions exploded showing the pedicle clamp of FIG. 1;

FIG. 3 is a plan view of the pedicle clamp of FIG. 1;

FIG. 4 is a drawing partially in section and partially in elevation of the pedicle clamp taken along line 4—4 of FIG. 1;

FIG. 5 is a drawing in section taken along line 5—5 of FIG. 1;

FIG. 6 is a schematic drawing showing two pedicle clamps of FIG. 1 attached to a vertebra;

DETAILED DESCRIPTION OF THE INVENTION

Figure 7:
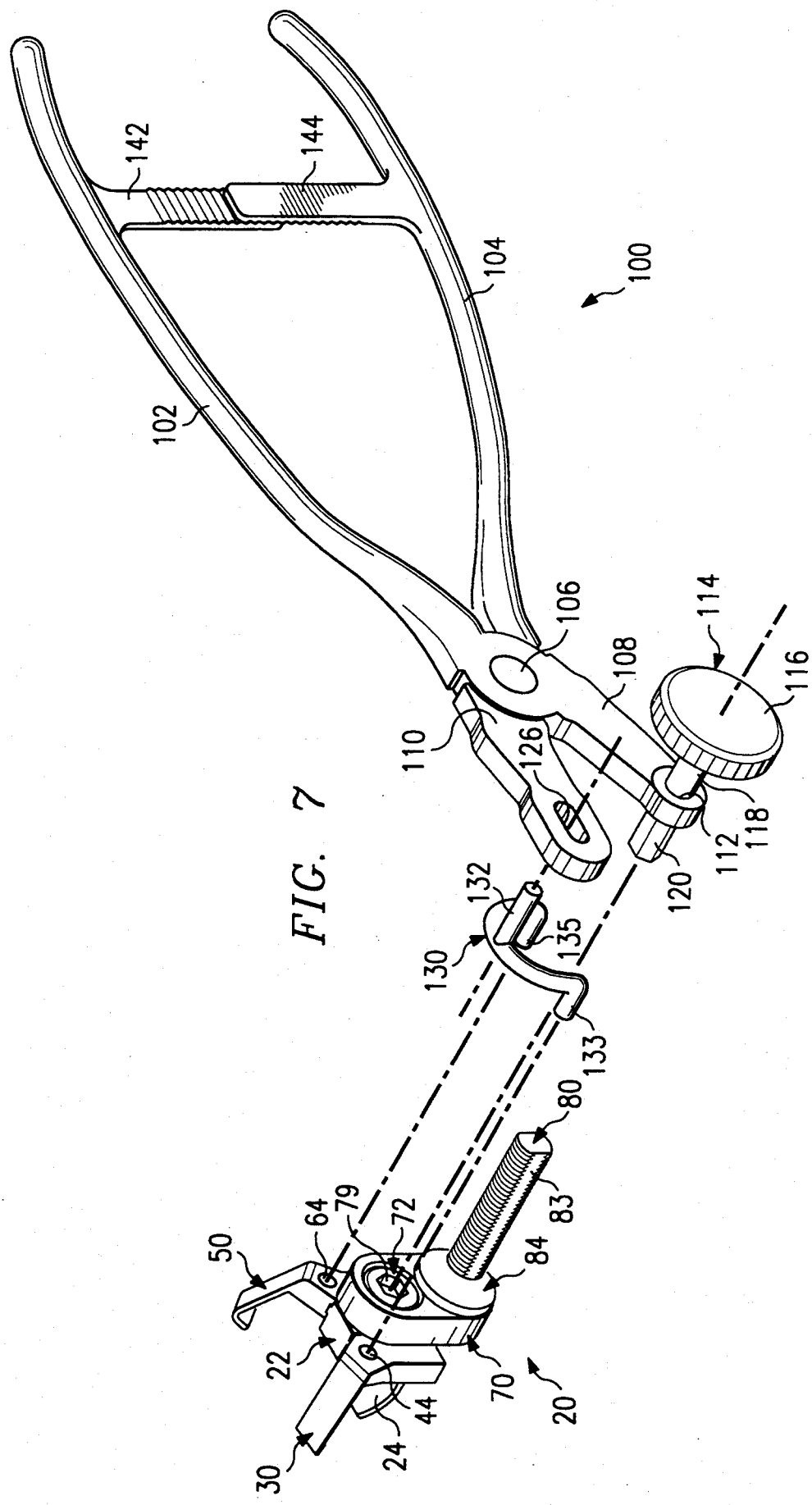
FIG. 7 is an isometric pictorial with portions broken away and other portions exploded showing surgical pliers modified for use in securing the pedicle clamp of FIG. 1 to selected portions of a patient's vertebra.

The preferred embodiments of the present invention and its advantages are best understood by referring to FIGS. 1 through 8 of the drawings, like numerals being used for like and corresponding parts of the various drawings.

A pedicle clamp 20 incorporating the present invention is shown in FIG. 1. The various components which comprise pedicle clamp 20 are attached to or carried by clamp body or body means 22. Fixed hook 24 extends from and is preferably formed as an integral part of clamp body 22. A pair of movable hooks 30 and 50 are slidably attached to clamp body 22. An important feature of the present invention is that pedicle clamp 20 has three hooks 24, 30 and 50 which cooperate with each other to releasably attach pedicle clamp 20 to selected vertebrae of a patient's spine.

Figure 8:
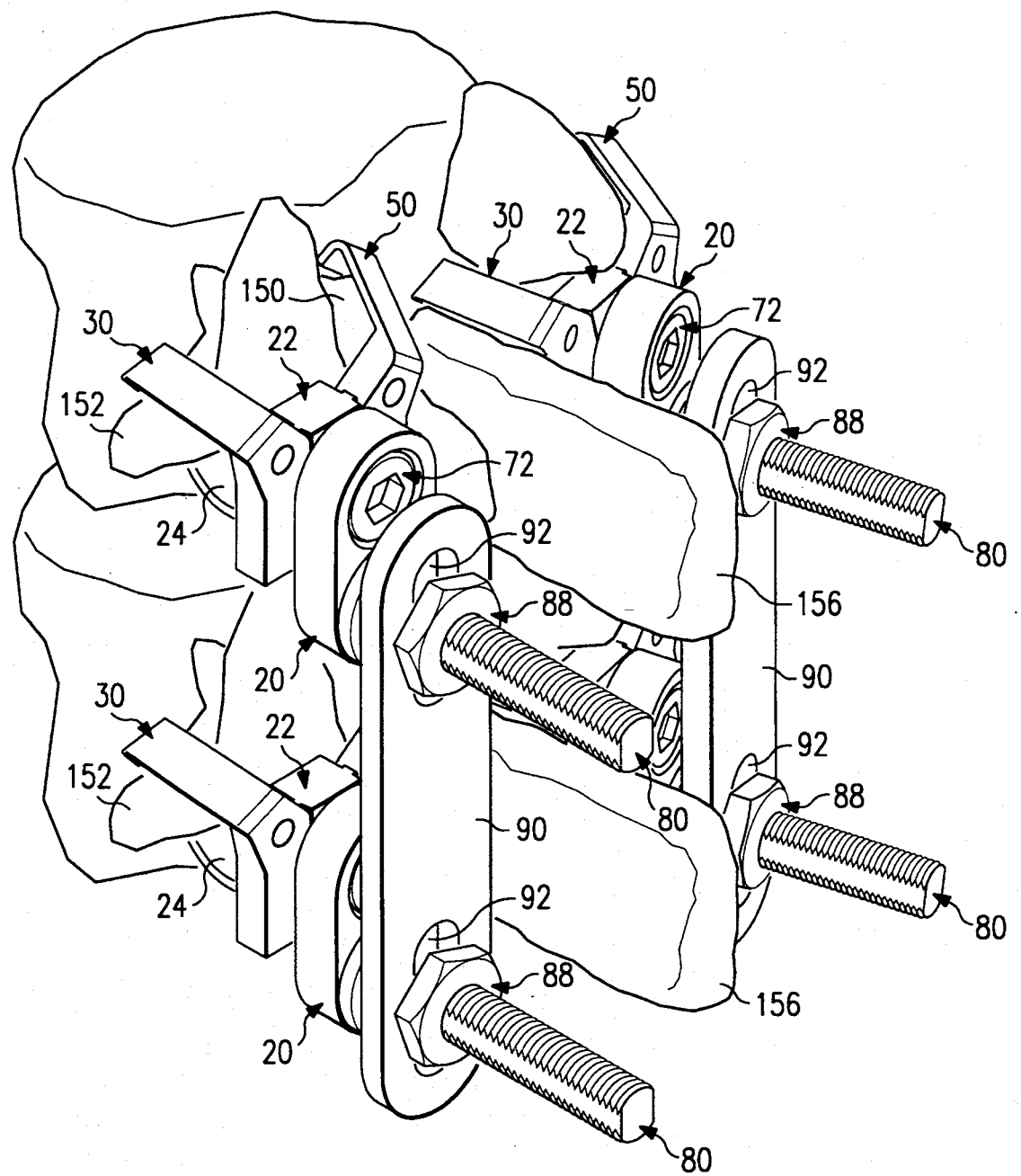
FIG. 8 is a schematic drawing in elevation with portions broken away showing a medical construct attached to selected portions of a patient's spine using the pedicle clamps of FIG. 1.

Pedicle clamp 20 is preferably installed posterior to the patient's spine as shown in FIGS. 6 and 8. Hooks 24, 30 and 50 are sized to engage selected portions of lamina 150, transverse process 152 and pedicle 154 on opposite sides of spinus process 156. During the surgical procedure, part of the facet or articulating process (not shown) may be removed to accommodate hooks 30 and 50. Removing the lower portion of the facet joint (not shown) will modify that portion of lamina 150 to accommodate hooks 30 and 50. Depending upon the condition of the selected vertebrae and the condition of the patient's spine, a portion of the transverse process 152 where it intersects with the facet joint, may also be removed as required for installation of pedicle clamp 20. By using three hooks 24, 30 and 50 which may be positioned relative to each other on posterior portions of the selected vertebra, pedicle clamp 20 may be securely anchored to the pedicle portion of the selected vertebra. Anchoring pedicle clamp 20 in this manner provides support for attaching spinal instrumentation comparable to the strength and support provided by pedicle screws. The present invention allows pedicle clamp 20 to engage the "isthmus" portion of the pedicle which is frequently the preferred location for attaching instrumentation to a patient's spine.

As best shown in FIGS. 2 and 5, movable hooks 30 and 50 are slidably attached to clamp body 22 by matching tongue and groove connections 26 and 36 for hook 30 and 26 and 56 for hook 50, respectively. The tongue and groove connections preferably have a dovetail configuration as shown in FIG. 5 to provide a tight interlocking joint between hooks 30 and 50 and clamp body 22. Tongues 26 on each side of clamp body 22 have the general configuration of a fan-shaped tenon and extend longitudinally on opposite sides of clamp body 22. The dovetail connections defined by tongues 26 and grooves 36 and 56 respectively cooperate with locking screw 72 to provide means for releasably locking movable hooks 30 and 50 relative to clamp body 22 and its associated fixed hook 24. If desired, grooves 36 and 56 may be formed in clamp body 22 and tongues 26 formed on hooks 30 and 50.

Movable hook 30 includes hook body 32 with curved arm 34 extending therefrom. The distance between end 38 of curved arm 34 and hook body 32 defines the gap dimension for movable hook 30. The throat dimension for movable hook 30 is defined in part by curved arm 34. Moveable hook 50 includes hook body 52 with curved arm 54 extending therefrom. As shown in FIG. 4, the distance from end 58 of curved arm 54 to hook body 52 defines gap dimension 60 for moveable hook 50. Throat dimension 62 for moveable hook 50 is defined in part by curved arm 54. The gap and throat dimensions for moveable hooks 30 and 50 may be identical. Alternatively, the gap and throat dimensions for each moveable hook 30 and 50 may be individually adjusted as required to properly engage selected portions of the patient's vertebrae.

Hole 44 in hook body 32 and hole 64 in hook body 52 are used to releasably anchor pedicle clamp 20 to selected portions of the patient's vertebrae. The function of holes 44 and 64 in cooperation with tongue and groove connection 26, 36 and 56 will be described later in more detail.

Connector 70 is attached to clamp body 22 by locking screw 72. Connector 70 has the general configuration of an oblong link with openings 74 and 76 extending therethrough. First opening 74 is sized to receive a head 78 of locking screw or cap screw 72. Second opening 76 is offset from first opening 74 and is sized to receive bridge screw or connecting post 80 therein. Clamp body 22 includes opening 23 sized to receive locking screw 72 extending through first opening 74. Matching threads are provided on the interior of opening 23 and the exterior of locking screw 72. Recess 75 is provided within first opening 74 to receive head 78 of locking screw 72. Opening 74, head 78 and recess 75 are sized to allow rotation of connector 70 relative to clamp body 22 prior to fully engaging locking screw 72 with opening 23. This configuration allows pedicle clamp 20 to be installed as a complete unit while at the same time providing flexibility in the positioning of connector 70 and connecting post 80 relative to clamp body 22.

Second opening 76 preferably has a reduced inside diameter portion 77 as shown in FIG. 4. Head 82 of connecting post 80 preferably includes a beveled exterior portion 97 which is sized to match with reduced inside diameter portion 77. Reduced inside diameter portion 77 and beveled surface 97 provide a portion of the mechanism to trap connecting post 80 within connector 70 while at the same time, allowing angular displacement of connecting post 80 with respect to connector 70. Beveled surface 97 and reduced inside diameter portion 77 preferably have matching radii of curvature to allow limited rotational and angular movement of connecting post 80 relative to connector 70.

Washer 84 with an exterior beveled surface 86 is used to secure connecting post 80 within second opening 76. Washer 84 preferably includes internal threads 87 which are compatible with threads 81 on the exterior of connecting post 80. Similar threads 89 are provided on the interior of nut 88. During installation of pedicle clamp 20, threads 87 in washer 84 are used to retain connecting post 80 within second opening 76 of connector 70. As best shown in FIGS. 2 and 4, connecting post 80 preferably includes a smooth, nonthreaded portion 85 immediately adjacent to beveled surface 97 of head 82. The longitudinal dimension of smooth surface 85 is such that threads 87 no longer engage threads 81 of connecting post 80 after connecting post 80 has been fully inserted into washer 84. This configuration allows limited angular movement of connecting post 80 within second opening 76 while at the same time retaining head 82 of connecting post 80 within second opening 76. The position of connecting post 80 may be varied substantially with respect to clamp body 22 by rotation of connector 70 prior to fully engaging locking screw 72 with opening 23 and by angular displacement of connecting post 80 within second opening 76.

After pedicle clamps 20 have been positioned as desired on selected portions of the patient's vertebrae, instrumentation such as spinal plate 90 may be positioned on each connecting post 80. As best shown in FIG. 8, nuts 88 may then be engaged with their respective connecting post 80 to position spinal plates 90 as desired relative to selected vertebrae. Flat surfaces 83 are preferably formed longitudinally on opposite sides of connecting post 80. Flat surfaces 83 are formed such that they do not hinder engagement of threads 87 in washer 84 and threads 89 in nut 88 with threads 81 on the exterior of connecting post 80.

Spinal plates 90 preferably include two or more longitudinal slots 92 extending through each spinal plate 90 to provide openings for installing the respective spinal plate 90 with the desired connecting posts 80. Flat surfaces 83 cooperate with longitudinal slots 92 to prevent rotation of connecting post 80 while tightening nut 88 with its respective connecting post 80. Prior to securely tightening nut 88 onto connecting post 80, beveled surfaces 97 and 77 cooperate to allow angular positioning of connecting post 80 relative to connector 70 and clamp body 22. If desired, beveled surfaces (not shown) may also be provided on one side of slots 92 to engage beveled surface 86 on washers 84. Nut 88 and washer 84 are used to secure connecting post 80 and spinal instrumentation such as spinal plates 90 in the desired position relative to the selected vertebrae.

Surgical tool 100 shown in FIG. 7 may be used to releasably anchor pedicle clamp 20 with selected portions of the patient's vertebrae. Surgical tool 100 has the general configuration of surgical pliers. Arms 102 and 104 are attached to each other by a pivot pin 106. A first jaw 108 is formed as part of arm 102 extending from pivot pin 106. A second jaw 110 is formed as part of arm 104 also extending from pivot pin 106. First jaw 108 includes an opening 112 with wrench 114 rotatably disposed therein. Wrench 114 includes an enlarged handle 116 which may be used to rotate wrench 114 within opening 112. Shaft 118 of wrench 114 extends through opening 112. The end of wrench 114 opposite from enlarged handle 116 has a hexagonally shaped head 120. Head 120 is preferably sized to be received within hexagonal opening 79 of locking screw 72.

Second jaw 110 has opening 126 extending therethrough. Opening 126 preferably has the configuration of an oblong, longitudinal slot sized to receive a portion of a fork 130 therein. Stem 132 of fork 130 is sized to be received within opening 126. Stem 132 and opening 126 cooperate to allow rotation of fork 130 with respect to second jaw 110 and limited longitudinal movement of fork 130 with respect to second jaw 110. Fork 130 includes two prongs 133 and 135. Prong 133 is sized to fit within opening 44 of movable hook 30. Prong 135 is sized to fit within opening 64 of movable hook 50. Arms 102 and 104 of surgical tool 100 preferably include alligator clips 142 and 144 which cooperate with each other to hold arms 102 and 104 in a desired position with respect to each other.

After placing hooks 24, 30 and 50 of pedicle clamp 20 on selected portions of the patient's vertebra, hexagonal head 120 of wrench 114 is positioned within hexagonal opening 79 of locking screw 72. Prongs 133 and 135 of fork 130 are positioned within their respective openings 44 and 64 of movable hooks 30 and 50. By manually squeezing arms 104 and 102, the desired amount of compression via jaws 108 and 110 may be placed on the lamina and pedicle portions of the vertebra disposed between hooks 24, 30 and 50.

When pedicle clamp 20 has been secured to the patient's vertebra with the desired amount of compressive force, alligator clips 142 and 144 cooperate to hold this compression. Wrench 114 may then be rotated using enlarged handle 116 to tighten locking screw 72 into opening 23 of clamp body 22. Locking screw 72 cooperates with clamp body 22 and dovetail grooves 36 and 56 to releasably anchor movable hooks 30 and 50 relative to fixed hook 24. After locking screw 72 has been properly tightened, arms 102 and 104 of surgical tool 100 may be released to allow removal of wrench 114 and fork 130 from pedicle clamp 20.

Pedicle clamps 20 will often be initially installed with only washer 84 used to loosely hold connecting post 80 within second opening 76 of connector 70. If desired, nut 88 may be placed on connecting post 80 prior to beginning the surgical procedure or while installing spinal plates 90.

Although the present invention and its advantages have been described in detail, it should be understood that various changes, substitutions and alterations can be made therein without departing from the spirit and scope of the invention as defined in the following claims.

What is claimed is:

1. A surgically implanted posterior spinal fixation system comprising:
   a plurality of pedicle clamps with each pedicle clamp having three hooks for attaching the respective pedicle clamps to selected vertebrae of a patient's spinel
   each of the pedicle clamps having a body means with one of the three hooks comprising a fixed hook extending therefrom from the body means:
   the three hooks further comprising a pair of movable hooks slidably attached to the body means; and
   means for releasably locking the pair of movable hooks to the respective body means.

2. The spinal fixation system as defined in claim 1 wherein the releasable locking means further comprises a locking screw engaged with a threaded opening in the body means.

3. The spinal fixation system as defined in claim 1 wherein each pedicle clamp further comprises:
   matching sets of tongues and grooves formed on the body means and each of the movable hooks;
   the tongues and grooves cooperating to provide a portion of the means for releasably locking the movable hooks to the body means; and a locking screw engaged with a threaded opening in the body means providing an additional portion of the means for releasably locking the movable hooks to the body means.

4. The spinal fixation system as defined in claim 3 wherein each pedicle clamp further comprises:
a connecting post and a connector having a first opening and a second opening longitudinally offset from each other;
the first opening sized to receive the locking screw therein;
the second opening sized to receive the connecting post therein; and
means for securing the connecting post to the connector.

5. The spinal fixation system as defined in claim 4 wherein each pedicle clamp further comprises:
a recess formed within the first opening of the connector; and
a head on the locking screw sized to engage the recess within the first opening whereby engaging the locking screw with the threaded opening in the body means releasably locks the movable hooks relative to the body means.

6. The spinal fixation system as defined in claim 4 wherein each pedicle clamp further comprises the body means having a longitudinal axis and the first opening in the connector sized to allow rotation of the connector relative to the longitudinal axis of the body means prior to releasably locking the movable hooks to the body means.

7. The spinal fixation system as defined in claim 6 further comprising means for attaching a spinal instrumentation to the connecting posts.

8. The spinal fixation system as defined in claim 6 further comprising means for attaching a spinal plate to the connecting posts.

9. The spinal fixation system as defined in claim 8 further comprising:
each connecting post having a head disposed within the second opening of the connector;
matching surfaces formed on the head of each connecting post and within the second opening to allow limited angular movement of the connecting post relative to the connector; and
means for securing the connecting post within the second opening.

10. The spinal fixation system as defined in claim 9 further comprising a flat surface formed longitudinally on the exterior of each connecting post.

11. The spinal fixation system as defined in claim 1 further comprising:
a first pair of pedicle clamps for attachment to the selected vertebrae on the posterior of one side of the patient's spine;
a second pair of pedicle clamps for attachment to the selected vertebrae on the posterior of the other side of the patient's spine;
a first elongated member for attachment with the first pair of pedicle clamps and extending posteriorly along the one side of the patient's spine; and
a second elongated member for attachment with the second pair of pedicle clamps and extending posteriorly along the other side of the patient's spine.

12. The spinal fixation system as defined in claim 11 wherein the elongated members further comprise spinal instrumentation.

13. The spinal fixation system as defined in claim 11 wherein the elongated members further comprise a pair of spinal plates.

14. A surgically implanted posterior spinal fixation system having a plurality of pedicle clamps with each pedicle clamp comprising:
a fixed hook extending therefrom;
a pair of movable hooks slidably attached thereto; and
means for releasably locking the movable hooks with respect to the fixed hook for attaching the respective pedicle clamp to a selected vertebrae of a patient's spine.

15. The spinal fixation system as defined in claim 14 wherein each pedicle clamp further comprises:
a connecting post and a connector having a first opening and a second opening longitudinally offset from each other;
the first opening sized to receive a locking screw;
the second opening sized to receive a connecting post therein; and
means for securing the connecting post to the connector.

16. The spinal fixation system as defined in claim 15 wherein each pedicle clamp further comprises:
the connecting post having a head disposed within the second opening of the connector;
matching surfaces formed on the head of the connecting post and within the second opening to allow limited angular movement of the connecting post relative to the connector; and
means for securing the connecting post within the second opening.

17. The spinal fixation system as defined in claim 16 further comprising a flat surface formed longitudinally on the exterior of the connecting post.

18. The spinal fixation system as defined in claim 16 wherein each pedicle clamp further comprises:
the connecting post further comprising a threaded portion and a smooth outside diameter portion adjacent to the head of the connecting post;
a washer having internal threads for engagement with the threaded portion of the connecting post; and
the smooth outside diameter portion of the connecting post sized to receive the washer and allow limited rotation and angular movement of the connecting post relative to the connector while retaining the connecting post within the second opening.

19. The spinal fixation as defined in claim 18 further comprising a plurality of nuts for engagement with the threaded portion of each connecting post to secure spinal instrumentation to the respective pedicle clamp.

20. A pedicle clamp for attaching a surgical construct to a selected portion of a patient's spine comprising:
a fixed hook and a pair of movable hooks for attaching the clamp to the selected portion of the patient's spine;
a clamp body with the fixed hook extending therefrom;
the pair of movable hooks slidably attached to the clamp body;
means for releasably locking the movable hooks relative to each other and the clamp body;
matching tongues and grooves on the exterior of the clamp body and the interior of each movable hook;

the tongues and grooves cooperating to provide a portion of the means for releasably locking the movable hooks to the clamp body; and a locking screw engaged with a threaded opening in the clamp body providing an additional portion of the means for releasably locking the movable hooks to the clamp body.

21. The pedicle clamp as defined in claim 20 further comprising:

a connecting post and a connector having a first opening and a second opening longitudinally offset from each other;

the first opening sized to receive the locking screw;

the second opening sized to receive the connecting post therein; and means for securing the connecting post to the connector.

22. The pedicle clamp as defined in claims 21 further comprising:

a recess formed within the first opening of the connector; and a head on the locking screw sized to engage the recess within the first opening whereby engagement of the locking screw with the threaded opening in the clamp body releasably locks the movable hooks relative to the clamp body.

23. The pedicle clamp as defined in claim 22 further comprising the first opening of the connector sized to allow rotation of the connector relative to the clamp body prior to releasably locking the movable hooks with the clamp body.

24. The pedicle clamp as defined in claim 23 further comprising means for attaching a spinal instrumentation to the connecting post.

25. The pedicle clamp as defined in claim 23 further comprising means for attaching a spinal plate to the connecting post.

26. The pedicle clamp as defined in claim 25 further comprising:

the connecting post having a head disposed within the second opening of the connector;

matching surfaces formed on the head of the connecting post and within the second opening to allow limited angular movement of the connecting post relative to the connector; and said means for securing the connecting post to the connector includes means for securing the connecting post within the second opening.

27. The pedicle clamp as defined in claim 21 further comprising the connecting post having an exterior and a flat surface formed longitudinally on the exterior of the connecting post.

* * * * *

UNITED STATES PATENT AND TRADEMARK OFFICE
CERTIFICATE OF CORRECTION

PATENT NO. : 5,415,659

DATED : May 16, 1995

INVENTOR(S) : Lee, et al

It is certified that error appears in the above-identified patent and that said Letters Patent is hereby corrected as shown below:

Column 6, line 50, after "patient's", delete "spinel" and insert -- spine; --.

Signed and Sealed this

Third Day of October, 1995

Attest:

BRUCE LEHMAN

Attesting Officer        Commissioner of Patents and Trademarks